United States Patent
Stanton et al.

(10) Patent No.: US 11,559,368 B2
(45) Date of Patent: Jan. 24, 2023

(54) DRAPE FOR AN IMAGING SYSTEM BASE AND LOWER GIMBAL

(71) Applicant: InSurgery, LLC, Lunenburg, MA (US)

(72) Inventors: Russell Stanton, Lunenburg, MA (US); Edward J. Daley, II, Maynard, MA (US)

(73) Assignee: InSurgery, LLC, Lunenburg, MA (US)

( * ) Notice: Subject to any disclaimer, the term of this patent is extended or adjusted under 35 U.S.C. 154(b) by 776 days.

(21) Appl. No.: 16/524,793

(22) Filed: Jul. 29, 2019

(65) Prior Publication Data

US 2020/0054409 A1 Feb. 20, 2020

Related U.S. Application Data

(60) Provisional application No. 62/765,263, filed on Aug. 20, 2018.

(51) Int. Cl.
  *A61B 46/10* (2016.01)
  *A61B 6/00* (2006.01)
  *A61B 6/03* (2006.01)

(52) U.S. Cl.
  CPC ............ *A61B 46/10* (2016.02); *A61B 6/4411* (2013.01); *A61B 6/4423* (2013.01); *A61B 6/032* (2013.01)

(58) Field of Classification Search
  CPC ......... A61B 6/0407; A61B 6/102; A61B 6/44; A61B 6/4411; A61B 6/4423; A61B 2017/00831; A61B 2017/00862; A61B 2017/00867; A61B 2017/00871; A61B 2017/00889; A61B 46/00; A61B 46/10; A61B 46/40; A61B 2050/0067; A61B 2050/0071; A61B 2050/0073; A61B 2050/0085; A61B 2050/3014; A61B 2560/04; A61B 2560/06; A61B 6/032; Y10S 128/14; Y10S 128/15; Y10S 128/917; Y10S 206/811; Y10S 292/11; Y10S 383/907; Y10S 606/90791
  See application file for complete search history.

(56) References Cited

U.S. PATENT DOCUMENTS 5,457,962 A * 10/1995 Faries, Jr. ............. A61B 46/10
                                                    128/849
5,778,891 A   7/1998 McMahan
                        (Continued)

FOREIGN PATENT DOCUMENTS

DE    10124490 B4 *  5/2005  ............. A61B 17/02
WO   2018171720 A1   9/2018

OTHER PUBLICATIONS

Written Opinion of the International Searching Authority, dated Oct. 25, 2019 for International Application No. PCT/US2019/045271, 6 pgs.

*Primary Examiner* — Chih-Cheng Kao
(74) *Attorney, Agent, or Firm* — Iandiorio Teska & Coleman, LLP

(57) ABSTRACT

Featured is a drape for an imaging system base slidably supporting a gimbal and gantry. The preferred drape includes a sheet configured to extend from a first end of the base, between the gimbal and the gantry, and to a second end of the base, one or more sleeves associated with the sheet, and one or more stretchable members (e.g., elastic cords) slidably disposed in said one or more sleeves and stretchable from the first end of the base to the second end of the base.

11 Claims, 9 Drawing Sheets

(56) References Cited

U.S. PATENT DOCUMENTS

| | | |
|---|---|---|
| 6,857,778 B2 | 2/2005 | Mun et al. |
| 8,770,839 B2 * | 7/2014 | Gregerson ............ G06F 3/0481 |
| | | 378/204 |
| 2003/0056698 A1 | 3/2003 | Comeaux |
| 2011/0281064 A1 | 11/2011 | Murphy et al. |
| 2013/0167847 A1 * | 7/2013 | Rogers ................ A61G 7/1051 |
| | | 294/81.1 |
| 2014/0041669 A1 | 2/2014 | Houde et al. |
| 2014/0332701 A1 * | 11/2014 | Byers ........................ G21F 3/00 |
| | | 250/519.1 |
| 2015/0114404 A1 * | 4/2015 | Czop ..................... A61B 46/10 |
| | | 128/856 |
| 2016/0338791 A1 | 11/2016 | Smith |
| 2017/0258544 A1 | 9/2017 | Osman |

* cited by examiner

DRAPE FOR AN IMAGING SYSTEM BASE AND LOWER GIMBAL

RELATED APPLICATIONS

This application claims benefit of and priority to U.S. Provisional Application Ser. No. 62/765,263 filed Aug. 20, 2018, under 35 U.S.C. §§ 119, 120, 363, 365, and 37 C.F.R. § 1.55 and § 1.78, which is incorporated herein by this reference.

FIELD OF THE INVENTION

This subject invention relates to drapes protecting the base and lower portion of the gimbal of an imaging system such as a computerized tomography (CT) machine.

BACKGROUND OF THE INVENTION

Imaging systems such as computerized tomography (CT) machines are often used during surgery. A typical CT machine (e.g., the Mobius Imaging, LLC "Airo" product) includes a gantry with a patient channel therethrough mounted to a gimbal itself mounted to a base. The gimbal can be moved linearly relative to the base. The base also includes a column supporting a patient table which can be moved linearly with respect to the column in and out of the gantry patient channel. See, for example, U.S. Pat. No. 8,770,839.

Sterility, of course, is extremely important in the operating theater. If a physician or nurse even touches a non-sterile surface or item, the health care professional must then leave the operating room, rescrub, and don new operating room attire.

Accordingly, drapes for imaging machines have been developed. For example, U.S. Published Patent Application No. 2011/0281064 (incorporated herein by this reference) discloses a drape for the patient channel of an imaging machine. The drape is in a form of a sleeve with elastic bands about each opening which are stretched over lips at the patient channel openings of the machine. See also WO2018/0171720 incorporated herein by this reference.

BRIEF SUMMARY OF THE INVENTION

Still, medical (e.g., saline) and/or patient (e.g., blood) fluids can contaminate the imaging system base. For example, the base may include channels, grooves, slots, and other features into which medical and/or patient fluids can be deposited. Thoroughly cleaning these features between surgeries can be difficult if not impossible and/or requires many man hours of labor. And, since the gimbal moves relative to the base during surgery, the gimbal would interfere with a sheet laid upon or taped to the base. Thus, the sheet could bunch up and then not adequately cover the base and/or cause a trip hazard.

Featured in one specific example, is a CT machine base sterile drape that stays in place as the gimbal moves relative to the base, which prevents surgical and/or patient fluid from contaminating the base, and which is easy to deploy before surgery and to remove after surgery. At the same time, the base drape is inexpensive to manufacture. One function of this drape is to reduce risk related to cross infection. During surgery, lots of human effluent pours down on the equipment below—including the base. This can be hard, and impractical to clean fully. The base drape mitigates this risk. It also reduces damage to the machine from attempts to clean it improperly.

Featured is a drape for an imaging system base slidably supporting a gimbal and gantry. The preferred drape includes a sheet configured to extend from a first end of the base, between the gimbal and the gantry, and to a second end of the base. One or more sleeves may be associated with the sheet and one or more stretchable members (e.g., elastic cords) are slidably disposed in the one or more sleeves and stretchable from the first end of the base to the second end of the base.

The drape may include first and second sleeves and first and second stretchable members, respectively, slidably disposed in the first and second sleeves and a third stretchable member connected to the first and second stretchable members on one end and connected on an opposite end to the first and second stretchable members via a fourth stretchable member connected to the first stretchable member and a fifth stretchable member connected to said second stretchable member.

The sheet may include a cutout for a patient table column associated with the imaging system. In this example, there may be sleeves disposed about the cutout and a stretchable member slidably disposed in each sleeve. There may be a hook on an end of one or more the stretchable members. The drape may further include a pad on the sheet. The drape may also further include one or more stay members associated with the sheet.

Also featured is a method of protecting an imaging system base from patient and/or surgical fluids. The preferred method includes extending a sheet from a first end of the base, between the system gimbal and gantry, and to a second end of the base, removably fastening the sheet to the first end of the base, and removably fastening the sheet to the second end of the base.

In one example, a drape for an imaging system base slidably supporting a gimbal and gantry includes a sheet configured to extend from a first end of the base, between the gimbal and the gantry, and then to a second end of the base, and means for tensioning the sheet and securing one end of the sheet to the first end of the base and for securing an opposite end of the sheet to the second end of the base.

The means for tensioning may include one or more stretchable members associated with the sheet. The bottom of the sheet may include one or more sleeves for the one or more stretchable members.

The subject invention, however, in other embodiments, need not achieve all these objectives and the claims hereof should not be limited to structures or methods capable of achieving these objectives.

BRIEF DESCRIPTION OF THE SEVERAL VIEWS OF THE DRAWINGS

Other objects, features and advantages will occur to those skilled in the art from the following description of a preferred embodiment and the accompanying drawings, in which.

DETAILED DESCRIPTION OF THE INVENTION

Figure 1:
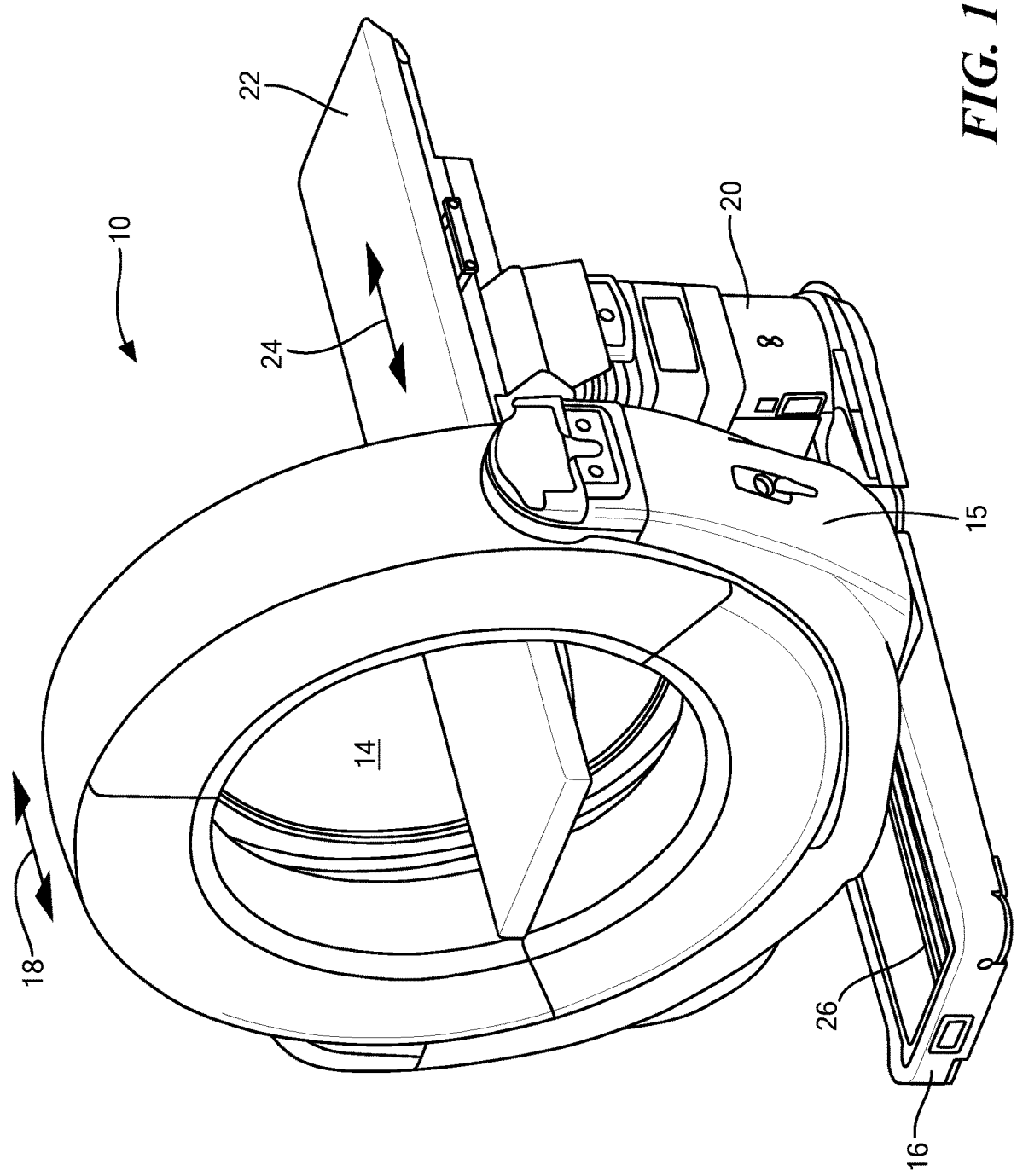
FIG. 1 is a schematic three dimensional view showing an example of an imaging system.

Aside from the preferred embodiment or embodiments disclosed below, this invention is capable of other embodiments and of being practiced or being carried out in various ways. Thus, it is to be understood that the invention is not limited in its application to the details of construction and the arrangements of components set forth in the following description or illustrated in the drawings. If only one embodiment is described herein, the claims hereof are not to be limited to that embodiment. Moreover, the claims hereof are not to be read restrictively unless there is clear and convincing evidence manifesting a certain exclusion, restriction, or disclaimer.

FIG. 1 shows an example of an imaging system 10 used in an operating room. Gantry 12 defines patient channel 14 and is mounted to gimbal 15 which moves relative to base 16 in the direction shown by arrow 18. Base 16 also may support column 20 supporting patient table 22 which moves relative to column 20 in the direction shown by arrow 24.

As noted previously, surgical and/or patient fluids can contaminate base 16 as, for example, the fluid pools in rails 26 and in other features of base 16. Fluid and/or particulates like bone fragments or hair can also contaminate and/or pool in the gimbal 15.

Figure 2:
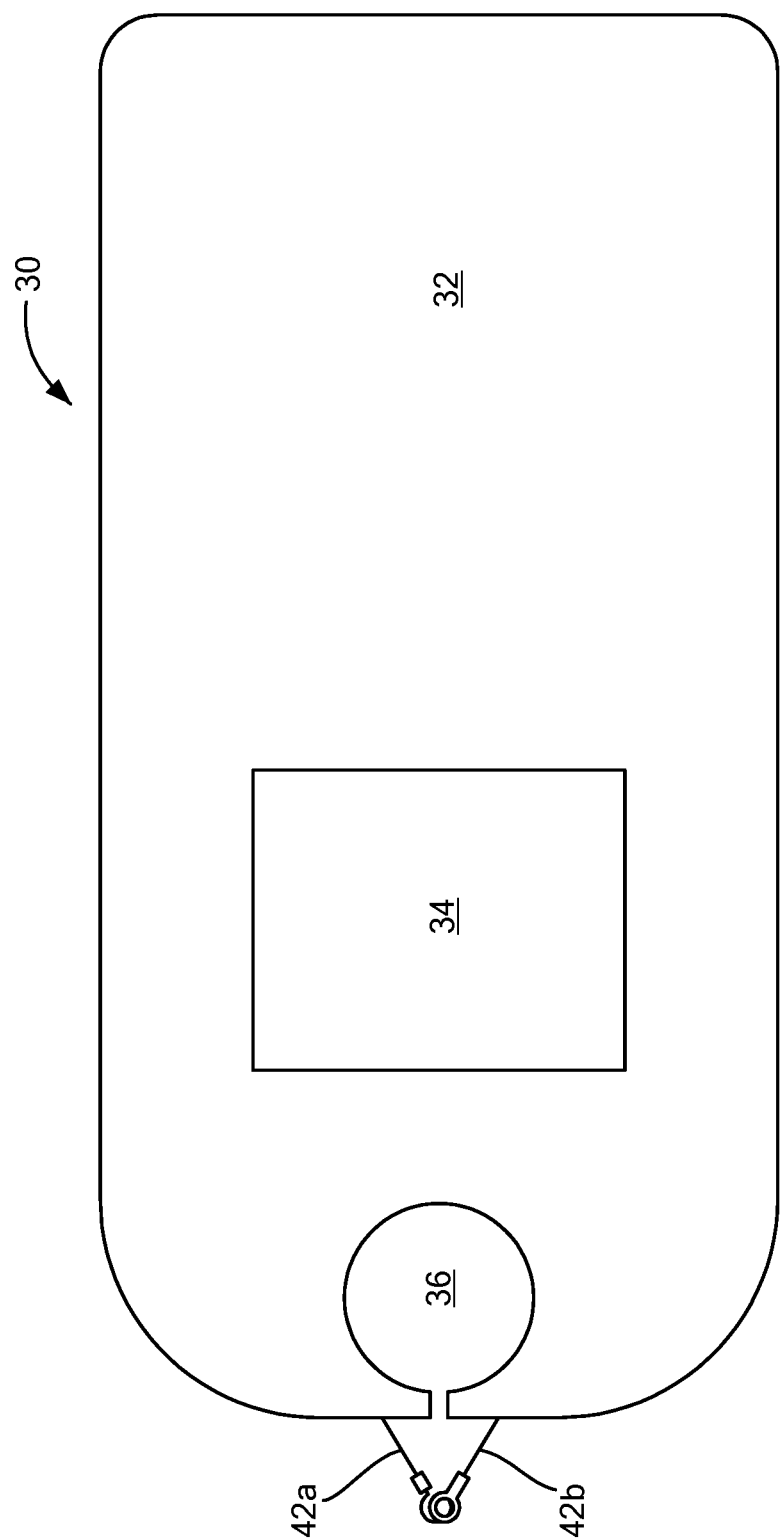
FIG. 2 is a top flattened view of an example of a drape for the base of the CT system of FIG. 1.
Figure 3:
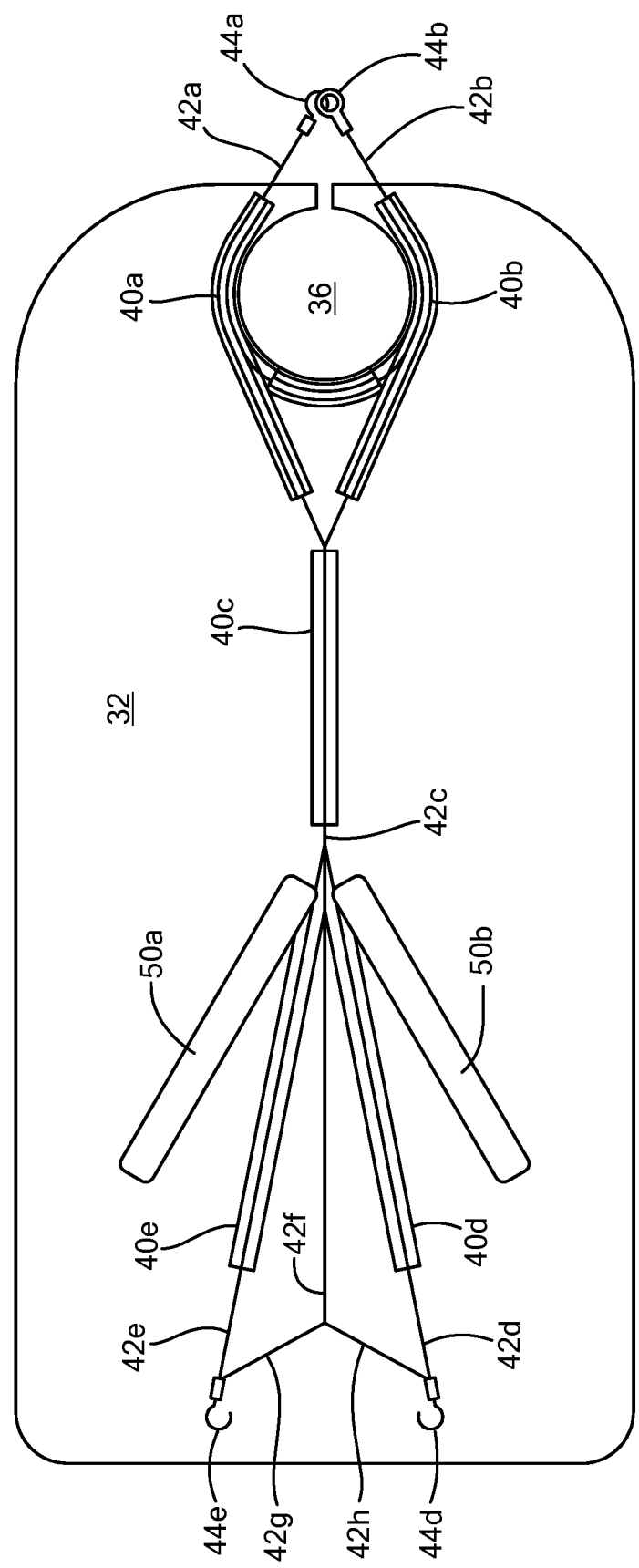
FIG. 3 is a bottom view of the drape of FIG. 2.

In one preferred embodiment, imaging system base drape 30, FIG. 2 includes a ply of protective material (e.g., a single ply of polyethylene) 32. Fabric may also be used. In some embodiments, multiple plies of material may make up the sheet. Absorbent and/or antimicrobial top pad 34 may be included. Round cutout 36 at one end of the sheet may be included for accommodating the patient table 22 column 20, FIG. 1. In other designs, the drape terminates before the column. In still other designs, the imaging system does not include a column. Bottom sleeves, 40a, 40b, 40c, 40d, and 40e, FIG. 3 are preferably included and typically are formed from a strip of plastic material welded or otherwise affixed to the bottom of sheet 32 as shown in FIG. 3. In this specific example, sleeves 40a and 40b are disposed about cutout 36, sleeve 40c is centrally disposed along the length of sheet 32, and sleeves 40d and 40e are at the opposite end of the sleeve. Corresponding stretchable members (e.g., elastic cords) 42a, 42b, 42c, 42d and 42e extend slidably in their respective sleeves 40a-40e. As shown, elastic cords 42a and 42b each include an end hook and/or eyelet 44a, 44b (and/or some other attachment mechanism) and are connected to elastic cord 42c which is connected to both elastic cords 42d and 42e which also includes corresponding end hooks 44d, 44e or some other fastening mechanism.

Also, it is preferred that additional elastic cord 42f is connected to elastic cord 42c on one end and to elastic cords 42g and 42h on the other end. The other end of elastic cords 42g and 42h, in turn, are connected to elastic cords 42e and 42d, respectively, and/or to hooks 44e and 44d, respectively. Other means for tensioning the drape sheet are possible.

Rigid (e.g., plastic) stays 50a, 50b may also be provided and attached to sheet 32 as shown in an angled fashion.

Figure 4:
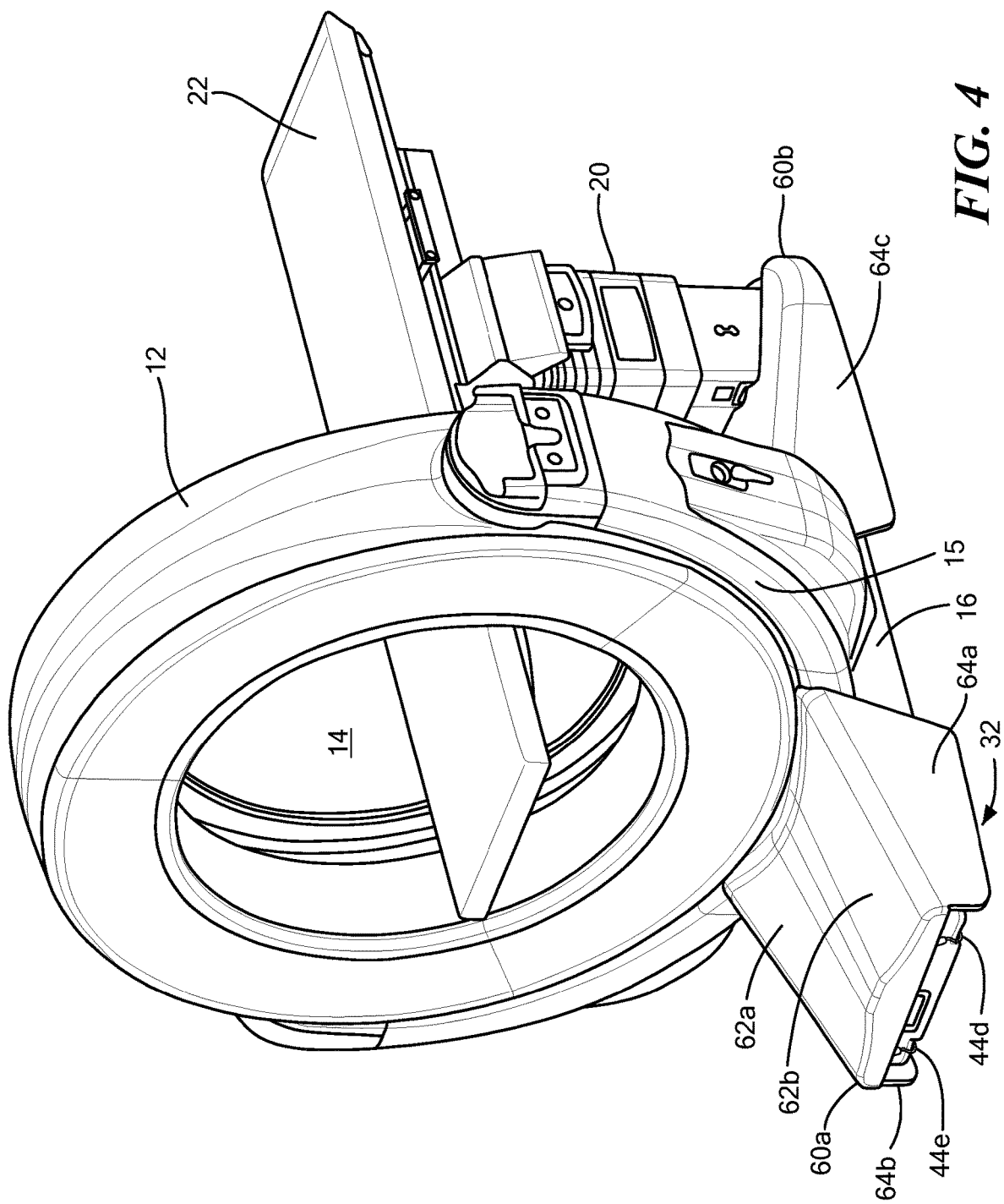
FIG. 4 is a schematic three dimensional view showing the drape of FIGS. 2 and 3 deployed onto the base of the CT system of FIG. 1.
Figure 5:
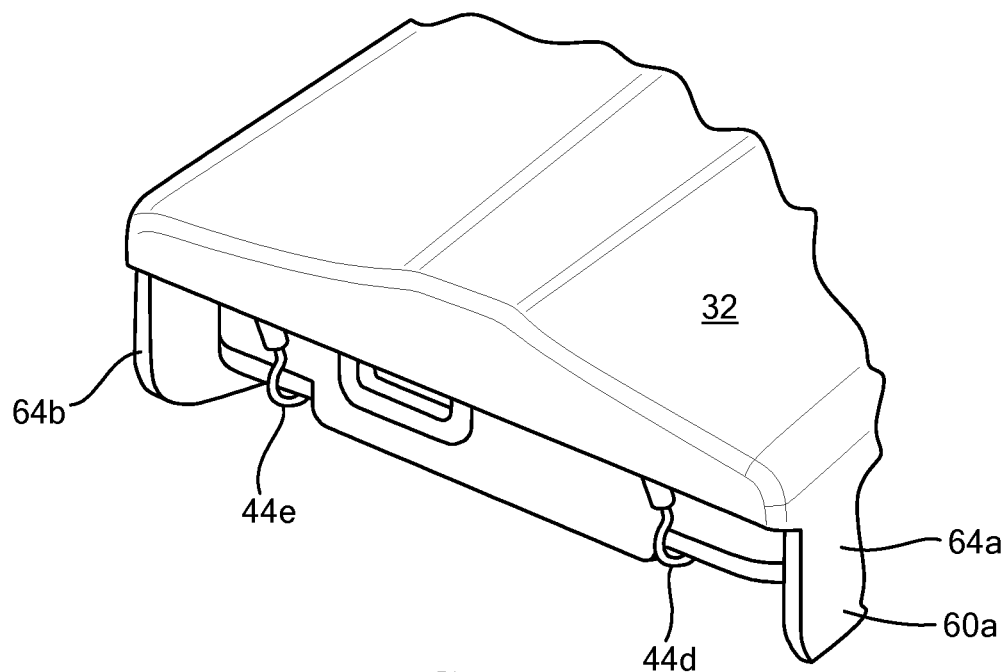
FIG. 5 is a partial three dimensional view showing the drape fastened to one end of the base of the CT system.
Figure 6:
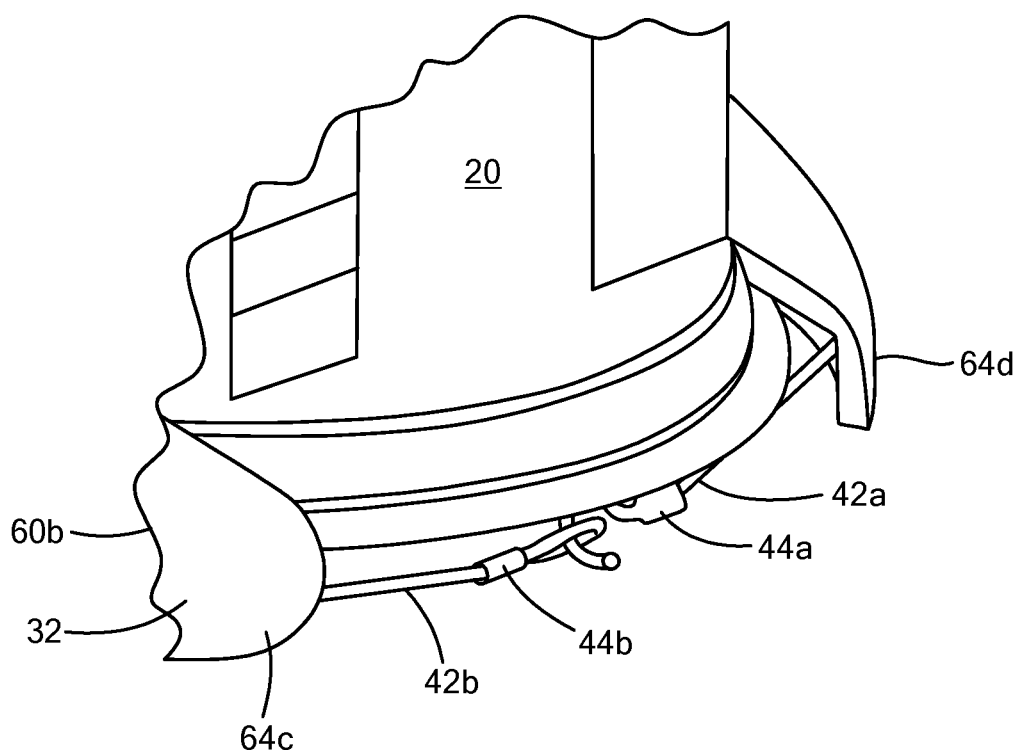
FIG. 6 is a schematic three dimensional view partial view showing the drape fastened to the other end of the CT system base.
Figure 7:
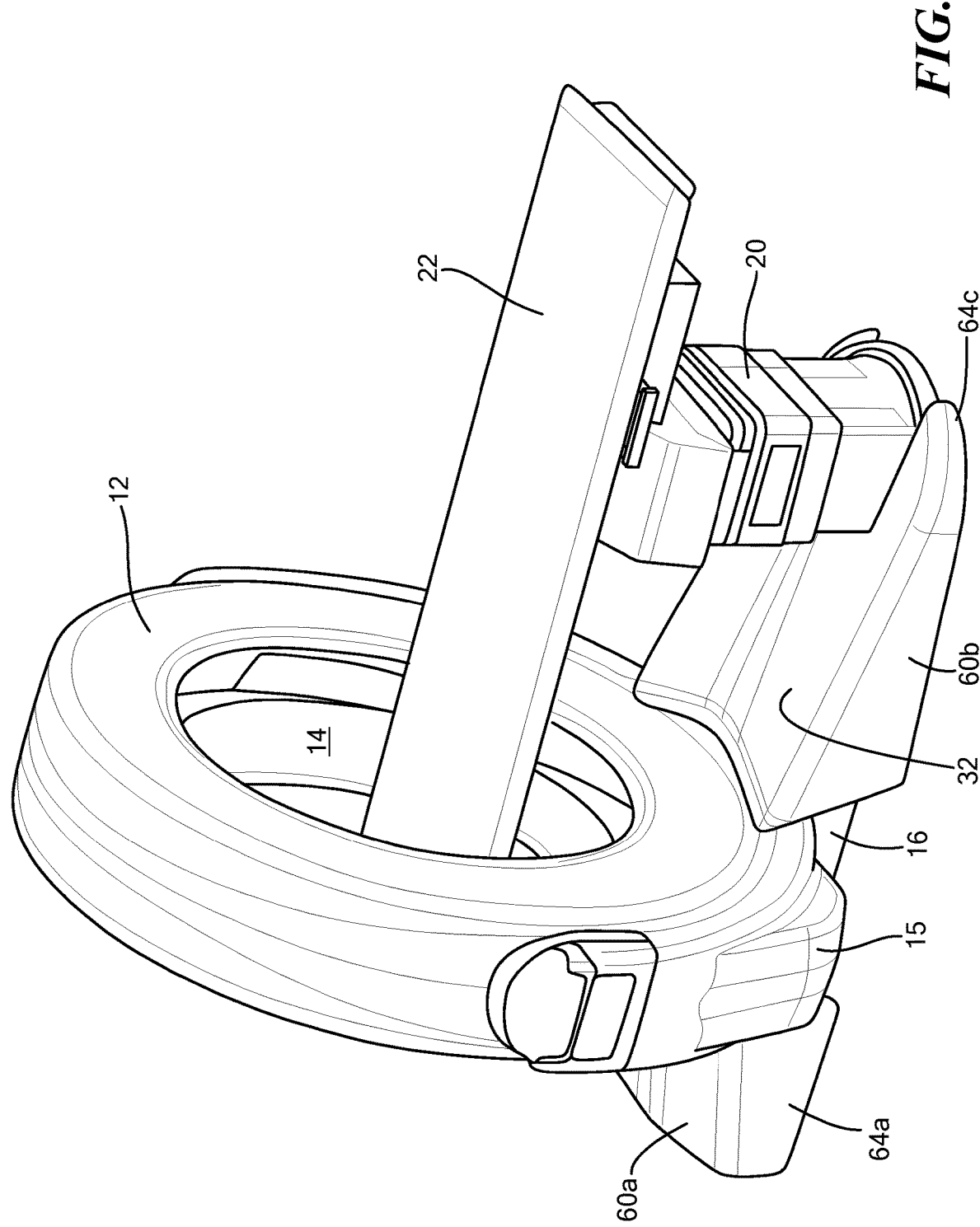
FIG. 7 is a another schematic three dimensional view showing the drape of FIGS. 2 and 3 deployed onto the CT system base of FIG. 1.
Figure 8:
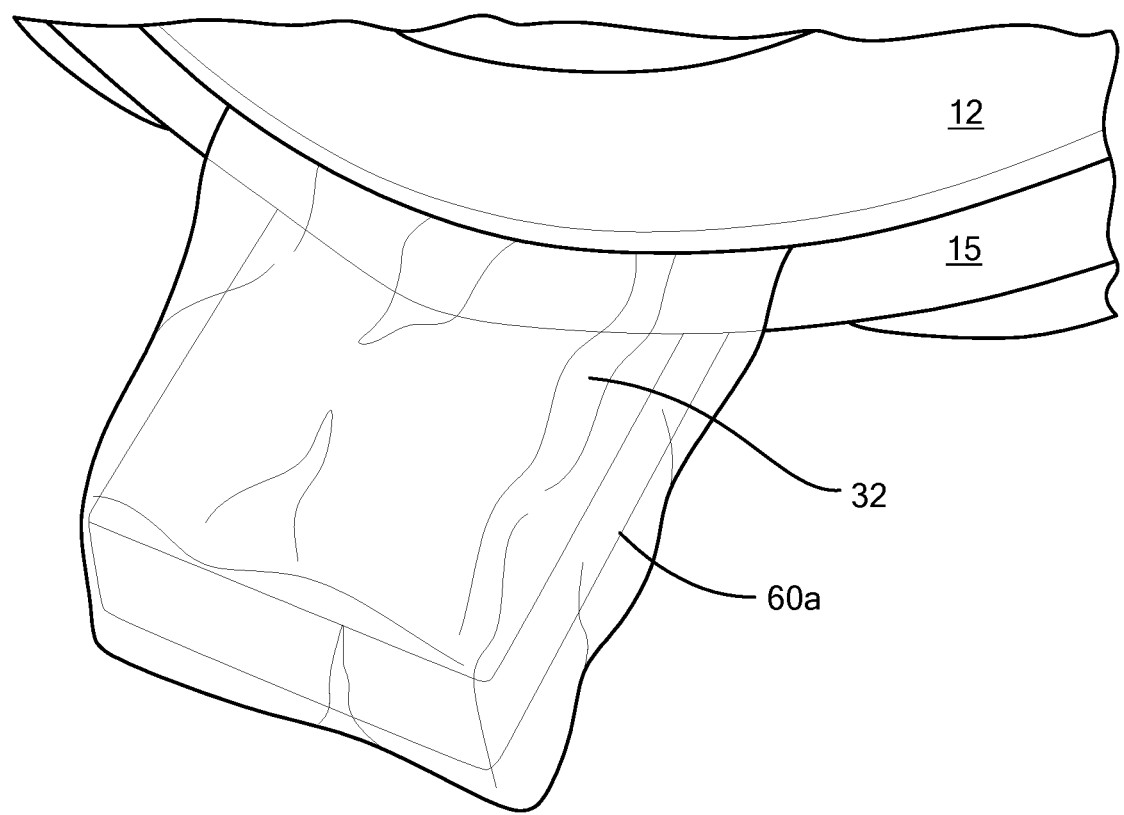
FIGS. 8-10 are schematic views showing an example of a deployed drape.
Figure 9:
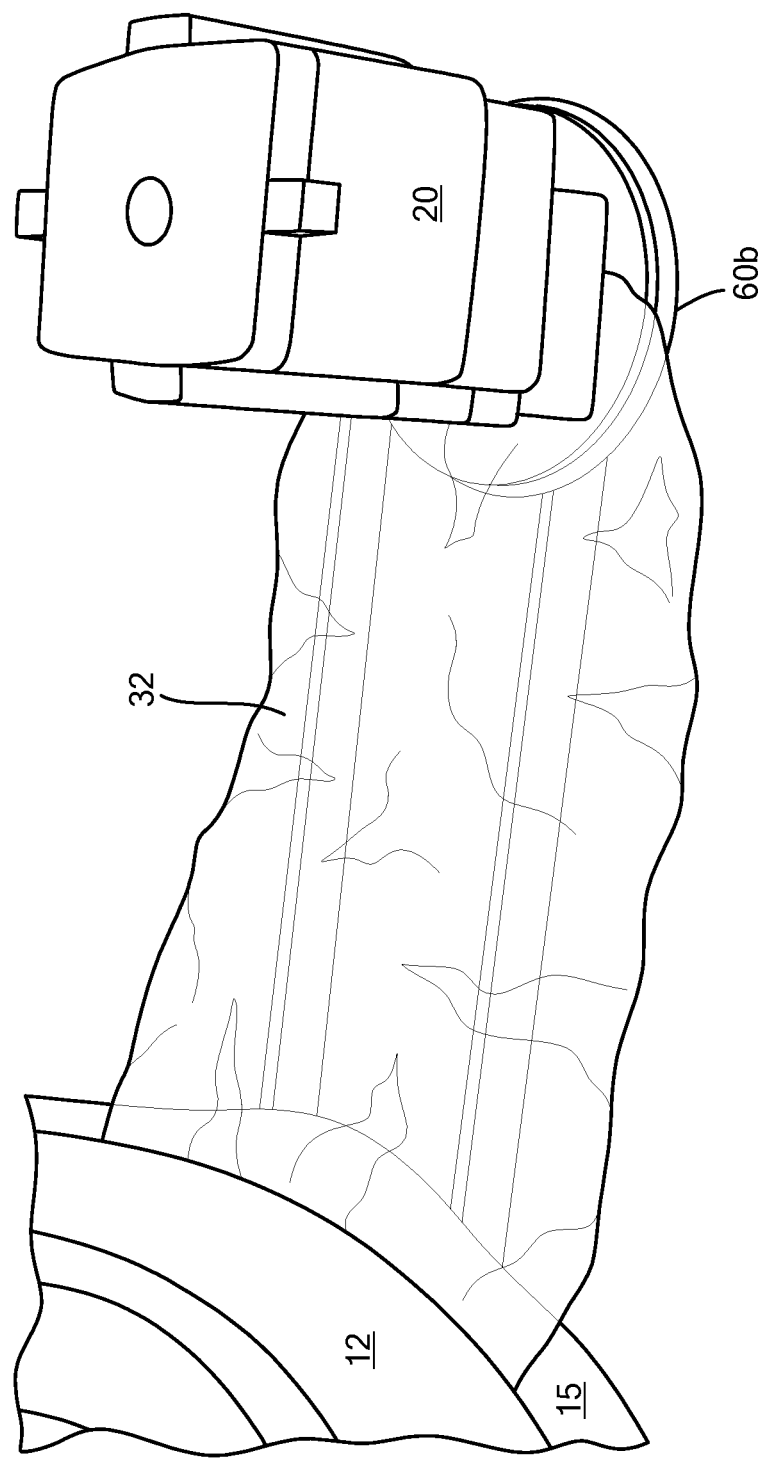
Figure 10:
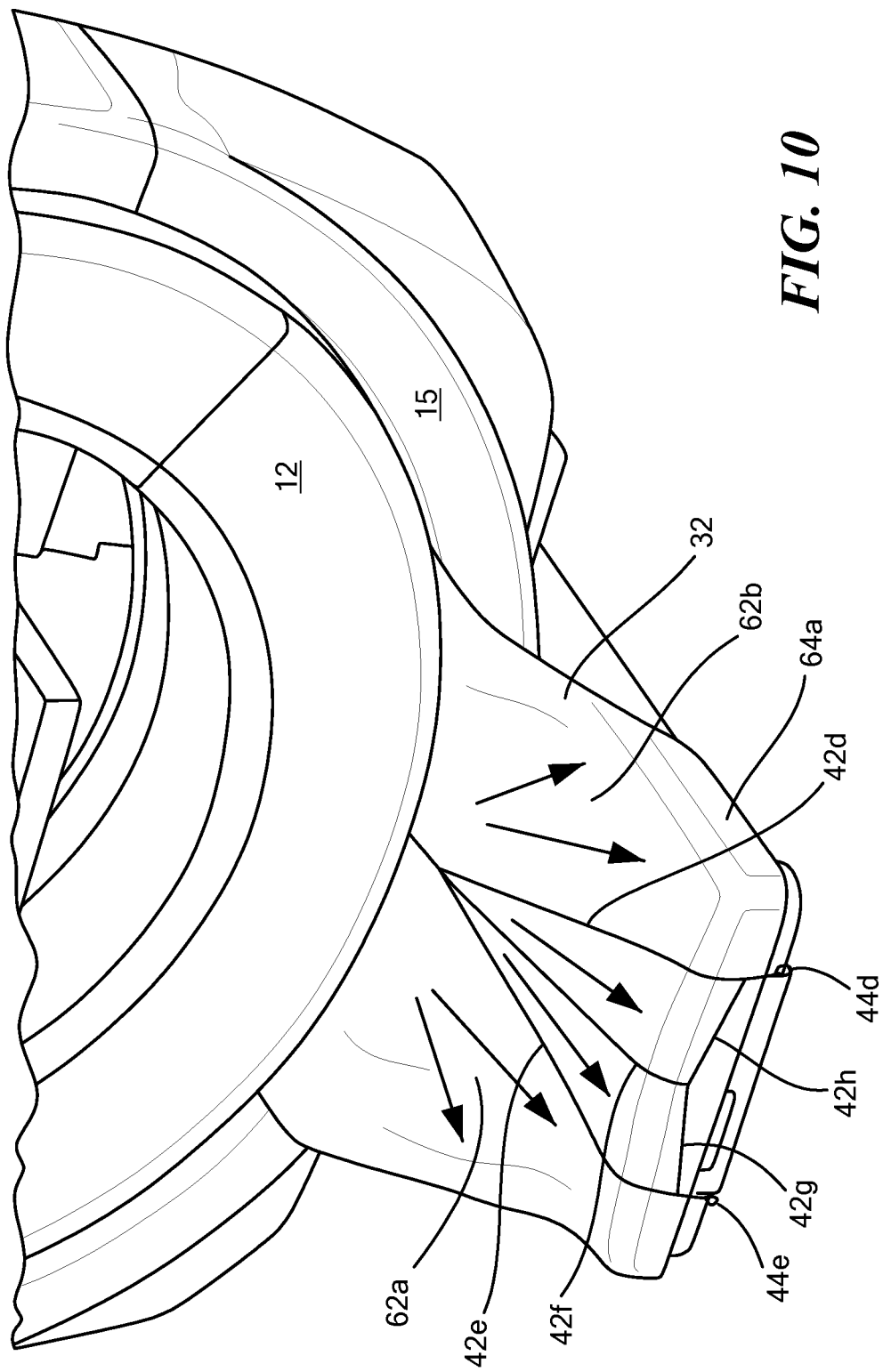

Accordingly, sheet 32 is configured to extend from end 60a, FIG. 4 of base 16 (see hooks 44d and 44e attached to base 16), through the narrow space between the lower end of gantry 12 and gimbal 15 (the semi-rigid stays 50a, 50b, FIG. 3, assist in threading the sheet through this space), and then over to the opposite end 60b of base 16 and around column 20 protecting the base against contamination by bodily and/or surgical fluids. The configuration of the elastic cords 42d-42g form downwardly sloping walls 62a, 62b, FIG. 4 which assist fluid in running off the sterile drape. The flexibility of the sterile drape enables it to form side walls 64a-64d. Other elastic cord configurations which form a tent like structure are possible, however. FIGS. 5-10 show how the elastic cord books and loops, in one example, are secured to each end 60a, 60b of the base.

Preferably, the polymeric sheet is fastened to the base of the machine using attachment hooks or similar hardware. The gantry will easily move over the polymeric sheet when a surgery is performed or during setup or tear-down. The attachment hooks attached to the ends of the elastic cords are hooked to specific locations on the base to tension, position, and secure the drape to the base. The absorbent anti-microbial pad may be fastened to the top of the polymeric sheet, positioned such that it contacts the bottom of the gantry when it passes over. This optional absorbent anti-microbial pad could be treated with anti-microbial fluid and will help clean the bottom of the gantry. The semi-rigid stays may be used during application of the drape. In one configuration, the drape is fed through a small slot between the gimbal and the gantry. The semi rigid stays aid in feeding the drape through this slot. However, these semi rigid stays may not be necessary if the gantry is tilted during drape application.

When applied properly, the base drape will protect the base and lower gimbal from falling fluids and debris. Runoff from the drape will be routed away from hard to clean areas of the base and gimbal to the floor surrounding the machine. The optional anti-microbial pad located on the top of the drape can be treated with a product of hospital choice to help clean the bottom of the gantry as it passes over the pad during surgery, setup, tear-down or service.

The drape is applied before surgery and after the machine is positioned in the operating room. The drape is removed from its packaging, laid on the floor at the end of the machine and unfolded. The semi-rigid stays are grasped and the drape is fed through the slot between the gimbal and gentry or the gantry is tilted to allow for easier drape application and positioning and the drape is laid on top of the gimbal and base. Once in position, the hook and eyes at the column end of the machine are attached to one another and positioned under the column base plate. The other end of the drape is then fastened to the base via the two hooks. Each of these hooks is secured to the base at the rear of the back caster pockets. Once secured to the base, the polymeric sheet is spread out to its maximum extents for optimal coverage.

After surgery, when the drape is to be removed, the drape should be cleared of all puddled fluids and easily removable debris. All hooks are unfastened and the drape is pulled away from the column, rolling or folding it then disposing of it properly.

The drape may be fabricated as any conventional polymeric medical grade drape material. Acceptable materials are selected and assembled using standard practices. Hot melt welding or adhesives are used in assembling the plastics and standard elastic cords are used with either custom designed or commercially available hooks. The anti-microbial pad is preferably an absorbent open cell foam or fibrous material capable of absorbing and holding fluids and is applied using standard adhesives.

The polymeric or similar material film or sheet is provided for protection of what lies beneath it. A method of securing the polymeric material is provided as well. In this specific design, hooks and elastic cord are used for this purpose. The semi-rigid stays and anti-microbial pad are both optional.

The drape could be either sterile or non-sterile. In another embodiment, the plastic or fabric material is inherently stretchable—thus perhaps eliminating the need for any cords. One example is an inexpensive thin sheet of Lycra that has a waterproof coating.

The drape can be configured with or without the anti-microbial pad or semi-rigid stays but preferably have a way of securing the polymeric or similar material to the base. The elastic cord could be replaced with non-elastic cord or straps or by simply attaching the drape to the base directly to the polymeric or similar material film. The drape could also be secured to the floor or features on the floor (e.g., Velcro, rings, hooks, and the like).

Although specific features of the invention are shown in some drawings and not in others, however, this is for convenience only as each feature may be combined with any or all of the other features in accordance with the invention. The words "including", "comprising", "having", and "with" as used herein are to be interpreted broadly and comprehensively and are not limited to any physical interconnection. Moreover, any embodiments disclosed in the subject application are not to be taken as the only possible embodiments. Other embodiments will occur to those skilled in the art and are within the following claims.

In addition, any amendment presented during the prosecution of the patent application for this patent is not a disclaimer of any claim element presented in the application as filed: those skilled in the art cannot reasonably be expected to draft a claim that would literally encompass all possible equivalents, many equivalents will be unforeseeable at the time of the amendment and are beyond a fair interpretation of what is to be surrendered (if anything), the rationale underlying the amendment may bear no more than a tangential relation to many equivalents, and/or there are many other reasons the applicant cannot be expected to describe certain insubstantial substitutes for any claim element amended.

What is claimed is:

1. A drape for aft a medical imaging system, said medical imaging system having a gantry mounted on a gimbal and wherein the gimbal slides along a support base of said medical imaging system, the drape comprising:
    a sheet configured to extend from a first position at a first end of the base, then between the gimbal and the gantry, and then to a second position at a second end of the base;
    one or more sleeves associated with the sheet; and
    one or more stretchable members slidably disposed in said one or more sleeves and stretchable from the first end of the base to the second end of the base.

2. The drape of claim 1 further comprising first and second sleeves, wherein the one or more stretchable members include first and second stretchable members both slidably disposed in said first and second sleeves, respectively, a third stretchable member connected to both said first and second stretchable members on one end of the third stretchable member, the third stretchable member connected on its opposite end to a fourth stretchable member which is connected to said first stretchable member, the third stretchable member also connected on its opposite end to a fifth stretchable member which is connected to said second stretchable member.

3. The drape of claim 1 wherein the sheet includes a cutout for a patient table column system coupled to the base support.

4. The drape of claim 3 further comprising sleeves disposed about the cutout and a stretchable member slidably disposed in each said sleeve.

5. The drape of claim 1 further comprising a fastening mechanism on an end of the one or more stretchable members.

6. The drape of claim 1 further comprising a pad on the sheet.

7. The drape of claim 1 further comprising one or more stay members associated with the sheet.

8. A method of protecting a support base of a medical imaging system from patient and/or surgical fluids, said medical imaging system having a gantry mounted on a gimbal and wherein the gimbal slides along the support base of the medical imaging system, the method comprising:
    extending a sheet from a first position at a first end of the base, then between the gimbal and gantry, and then to a second position at a second end of the base;
    removably fastening the sheet to the first end of the base; and
    removably fastening the sheet to the second end of the base.

9. A drape for a medical imaging system, said medical imaging system having a gantry mounted on a gimbal and wherein the gimbal slides along a support base of said medical imaging system, the drape comprising:
    a sheet configured to extend from a first position at a first end of the base, then between the gimbal and the gantry, and then to a second position at a second end of the base; and
    means for tensioning the sheet and securing one end of the sheet to the first end of the base and securing an opposite end of the sheet to the second end of the base.

10. The drape of claim 9 further comprising the means for tensioning including one or more stretchable members.

11. The drape of claim 10 further comprising one or more sleeves attached to the bottom of the sheet wherein the one or more sleeves enclose the one or more stretchable members.

* * * * *